US012109265B2

(12) United States Patent
Kauvar et al.

(10) Patent No.: US 12,109,265 B2
(45) Date of Patent: *Oct. 8, 2024

(54) DRUG REGIMEN FOR TREATMENT OF CEREBRAL ISCHEMIA

(71) Applicant: Shimojani, LLC, Pray, MT (US)

(72) Inventors: Lawrence M. Kauvar, San Francisco, CA (US); Damir Janigro, Cleveland Heights, OH (US)

(73) Assignee: Shimojani, LLC, Pray, MT (US)

( * ) Notice: Subject to any disclaimer, the term of this patent is extended or adjusted under 35 U.S.C. 154(b) by 119 days.

This patent is subject to a terminal disclaimer.

(21) Appl. No.: 17/392,144

(22) Filed: Aug. 2, 2021

(65) Prior Publication Data

US 2021/0361769 A1    Nov. 25, 2021

Related U.S. Application Data

(60) Division of application No. 16/842,458, filed on Apr. 7, 2020, which is a continuation of application No. 15/859,075, filed on Dec. 29, 2017, now Pat. No. 10,617,756.

(60) Provisional application No. 62/470,086, filed on Mar. 10, 2017, provisional application No. 62/442,826, filed on Jan. 5, 2017.

(51) Int. Cl.
| | | |
|---|---|---|
| C07K 16/22 | (2006.01) | |
| A61K 38/49 | (2006.01) | |
| A61K 39/395 | (2006.01) | |
| A61P 9/10 | (2006.01) | |
| G01N 33/49 | (2006.01) | |

(52) U.S. Cl.
CPC .......... *A61K 39/3955* (2013.01); *A61K 38/49* (2013.01); *A61P 9/10* (2018.01); *C07K 16/22* (2013.01); *G01N 33/491* (2013.01); *C12Y 304/21031* (2013.01); *C12Y 304/21068* (2013.01); *C12Y 304/21073* (2013.01)

(58) Field of Classification Search
CPC ....... A61K 39/3955; A61K 38/49; A61P 9/10; G01N 33/491; C07K 16/22; C12Y 304/21068; C12Y 304/21073; C12Y 304/21031
See application file for complete search history.

(56) References Cited

U.S. PATENT DOCUMENTS

| | | |
|---|---|---|
| 4,976,959 A | 12/1990 | Berger et al. |
| 5,766,520 A | 6/1998 | Bronshtein |
| 6,884,591 B2 | 4/2005 | Janigro et al. |
| 7,144,708 B2 | 12/2006 | Janigro et al. |
| 7,153,472 B1 | 12/2006 | Bronshtein |
| 8,313,897 B2 | 11/2012 | Drew |
| 8,652,476 B2 | 2/2014 | Shimohata et al. |
| 9,439,961 B2 | 9/2016 | Shimohata et al. |
| 9,913,899 B2 | 3/2018 | Kauvar et al. |
| 10,617,756 B2 | 4/2020 | Kauvar et al. |
| 11,077,188 B2 | 8/2021 | Kauvar et al. |
| 2003/0133972 A1 | 7/2003 | Danthi |
| 2005/0053599 A1 | 3/2005 | Van Bruggen et al. |
| 2005/0130230 A1 | 6/2005 | Davalos et al. |
| 2007/0258980 A1 | 11/2007 | Van Bruggen et al. |
| 2009/0123452 A1 | 5/2009 | Madison |
| 2009/0285826 A1 | 11/2009 | Bonnel et al. |
| 2012/0189631 A1 | 7/2012 | Shimohata et al. |
| 2014/0127233 A1 | 5/2014 | Shimohata et al. |
| 2015/0258193 A1 | 9/2015 | Kauvar et al. |
| 2018/0185475 A1 | 7/2018 | Kauvar et al. |
| 2020/0230237 A1 | 7/2020 | Kauvar et al. |

FOREIGN PATENT DOCUMENTS

| | | | |
|---|---|---|---|
| JP | 63-22026 | 1/1988 | |
| JP | 2011-046684 | 3/2011 | |
| JP | 2011-046685 | 3/2011 | |
| WO | WO-1997/015323 | 5/1997 | |
| WO | WO-2000/037502 | 6/2000 | |
| WO | WO-2004/096268 | 11/2004 | |
| WO | WO-2009033743 A1 * | 3/2009 | ............. C07K 16/18 |
| WO | WO-2011/013668 | 2/2011 | |
| WO | WO-2012/154889 | 11/2012 | |
| WO | WO-2015/138974 | 9/2015 | |
| WO | WO 2018/129206 | 7/2018 | |

OTHER PUBLICATIONS

Kanazawa et al (J Cereb Blood Flow Metab 31: 1461-1474, 2011) (Year: 2011).*
Zuo et al. Increased Risk of Cerebrovascular Events in Patients with Cancer Treated with Bevacizumab: A Meta-Analysis. PLoS One. 2014; 9(7): e102484) (Year: 2014).*
Almagro and Fransson, "Humanization of Antibodies" Frontiers in Bioscience (2008) 13:1619-1633.
Anonymous: "VEGF Signaling Pathway—Cusabio", Sep. 21, 2017 (Sep. 21, 2017), XP055815280, Retrieved from the Internet: URL:https://www.cusabio.com/pathway/VEGF-signaling-pathway.html [retrieved on Jun. 17, 2021].
Avery et al., "Systemic pharmacokinetics following intravitreal injections of ranibizumab, bevacizumab or aflibercept in patients with neovascular AMO," British Journal of Ophthalmology (2014) 98(12):1636-1641.

(Continued)

*Primary Examiner* — Kimberly Ballard
*Assistant Examiner* — Aditi Dutt
(74) *Attorney, Agent, or Firm* — Morrison & Foerster LLP

(57) ABSTRACT

Treatment of subjects experiencing cerebral ischemia is improved when the treatment employs a thrombolytic and an inhibitor against vascular endothelial growth factor receptor signal transduction (VEGF-RST) at a reduced, low dosage compared to that used to treat cancer patients. The treatment is also improved to permit point-of-care use by formulating protein drugs for long term stability at room temperature, providing doses appropriate for the method, and by combining the therapeutic agents with a point-of-care diagnostic for blood brain barrier integrity.

11 Claims, No Drawings

(56) References Cited

OTHER PUBLICATIONS

Baeuerle et al., "Bispecific T-Cell Engaging Antibodies for Cancer Therapy" Cancer Research (2009) 69(12):4941-4944.
Bambace et al., "The effect of P2Y-mediated platelet activation on the release of VEGF and endostatin from platelets" Platelets (2010) 21 (2):85-93.
Benhar, "Design of synthetic antibody libraries" Expert Opin. Biol. Ther. (2007) 7(5):763-779.
Chiba et al., "Anti-VEGF receptor antagonist (VGA 1155) reduces infarction in rat permanent focal brain ischemia," Kobe J Med Sci (2008) 54(2):E136-E146.
Chiba, "Effect of anti-VEGF receptor antagonist(VGA 1155) after middle cerebral artery occlusion in rats" Annual Meeting of the Japan Neurosurgical Society Abstract (2007) 66:1 K-P01-1-2.
Chica et al., "Semi-rational approaches to engineering enzyme activity: combining the benefits of directed evolution and rational design," Curr. Opin. Biotechnol. (2005) 16(4):378-384.
Chu, "Aflibercept (AVE0005): an alternative strategy for inhibiting tumour angiogenesis by vascular endothelial arowth factors" Expert Opin. Biol. Ther. (2009) 9(2):263-271.
Collarini et al., "Potent High-Affinity Antibodies for Treatment and Prophylaxis of Respiratory Syncytial Virus Derived from B Cells of Infected Patients" Journal of Immunology (2009) 183:6338-6345.
Dassan et al., Criteria for a clinically informative serum biomarker in acute ischaemic stroke: A review of S1 OOB.
Del Zoppo et al., "Expansion of the Time Window for Treatment of Acute Ischemic Stroke With Intravenous Tissue Plasminoqen Activator," Stroke (2009) 40:2945-2948.
Deschacht et al., "A Novel Promiscuous Class of Camelid Single-Domain Antibody Contributes to the Antigen-Binding Repertoire" Journal of Immunology (2010) 184:5696-5704.
Ebinger et al., "Effect of the use of ambulance-based thrombolysis on time to thrombolysis in acute ischemic stroke: a randomized clinical trial," JAMA (2014) 311 (16):1622-1631.
Fagan et al., "Targets for vascular protection after acute ischemic stroke," Stroke (2004) 35:2220-2225.
Fitchett, "The impact of bleeding in patients with acute coronary syndromes: how to optimize the benefits of treatment and minimize the risk" Can. J. Cardiol. (2007) 23(8):663-671.
Guo et al., "Cell-Selex: Novel Perspectives of Aptamer-Based Therapeutics" International Journal of Molecular Sciences (2008) 9:668-678.
Hacke et al., "Thrombolysis with Alteplase 3 to 4.5 Hours after Acute Ischemic Stroke," The New Enqland Journal of Medicine (2008) 359(13):1317-1329.
Hansen et al., "Vascular endothelial growth factor and angiopoietins in neurovascular regeneration and protection following stroke," Curr Neurovasc Res. (2008) 5(4):236-45.
Herrmann et al. "Release of glial tissue specifc proteins after an acute stroke: A comparative analysis of seum concentrations of protein S-100B and glial fibrillary acidic protein" Stroke (2000) 31(11):2670-2677.
Holtzman et al., "Miniature protein ligands for EVH1 domains: Interplay between affinity, specificity, and cell motility" Biochemistry (2007) 46(47):13541-13553.
Jakobovits et al., "From XenoMouse technology to panitumumab, the first fully human antibody product from transgenic mice" Nature Biotechnology (2007) 25(10):1134-1143.
Kanazawa et al., "Inhibition of VEGF signaling pathway attenuates hemorrhage after tPA treatment," J Cereb Blood Flow Metab (2011) 31 (6):1461-1474.
Kanazawa et al., "VEGF Expression of Vascular Endothelial Cells in Middle Cerebral Artery Occlusion Rat Models" Program and Abstracts of the Meeting of the Japanese Society of Neurology (2008) 49:267.
Kimura et al., "Brain Protective Effect of VEGF-Neutralizing Antibody Against Cerebral Venous Infarction" Jomyaku (2004) 115(2):155 B-22.

Kimura et al., "Cerebroprotective Effects of VEGF Neutralizing Antibody on Cerebral Venous Infarction," (2004) 15(2):155(8-22) (Enqlish abstract included).
Kimura et al., "Vascular endothelial growth factor antagonist reduces brain edema formation and venous infarction," Stroke (2005) 36(6):1259-1263.
Kumai et al., "Postischemic gene transfer of soluble Flt-1 protects against brain ischemia with marked attenuation of blood-brain barrier permeability" J Cerebral Blood Flow Metab (2007) 27:1152-1160.
Kutchukian et al., "All-Atom Model for Stabilization of a-Helical Structure in Peptides by Hydrocarbon Staples" Journal of the American Chemical Society (2009) 131 :4622-4627.
Luka et al., "Microfluidics Integrated Biosensors: A Leading Technology towards Lab-on-a-Chip and Sensing Applications," Sensors (2015) 15(12):30011-30031.
Lunsberg et al., "Efficacy and Safety of Tissue Plasminogen Activator 3 to 4.5 Hours After Acute Ischemic Stroke," Stroke (2009) 40:2438-2441.
Marchi et al., "Peripheral markers of brain damage and blood-brain barrier dysfunction," Res Neural Neurosci (2003) 21 (3):109-121.
Minematsu, "New progress of thrombolytic therapy," Int Rev Thrombosis (2008) 3(3):262-266 (English abstract included).
Morris, "RNA-Directed Transcriptional Gene Silencing and Activation in Human Cells" Oliqonucleotides (2009) 19(4):299-305.
Murray et al., "The molecular basis of thrombolysis and its clinical application in stroke" Journal of Internal Medicine (2010) 267:191-208.
Nagai et al., "Comparative effects of tissue plasminogen activator, streptokinase, and staphylokinase on cerebral ischemic infarction and pulmonary clot lysis in hamster models," Circulation (1999) 100:2541-2546.
Novitzky et al., "Comparison of Neuroprotective Effect of Bevacizumab and Sildenafil following Induction of Stroke in a Mouse Model," Biomed Research International (2016) p. 1-8.
Petersson and Schepartz, "Toward 13-Amino Acid Proteins: Design, Synthesis, and Characterization of a Fifteen Kilodalton 13-Peptide Tetramer" Journal of the American Chemical Society (2008) 130:821-823.
Puvenna et al., "Significance of Ubiquitin Carboxy-Terminal Hydrolase L 1 Elevations in Athletes after Sub-Concussive Head Hits," PLoS One (2014) 9(5):e96296.
Rubin et al., "What to do With Wake-Up Stroke," Neurohospitalist (2015) 5(3):161-172.
Sato, "Anti-angiogenic drugs," Japan J Cancer Chemother (2009) 36(7):1072-1075.
Seffernick et al., "Melamine deaminase and atrazine chlorohydrolase: 98 percent identical but functionally different," J. Bacteriol. (2001) 183(8):2405-2410.
Shimohata et al., "Neuro-Vascular Protection Therapy in the Post t-PA Age" Niigata Medical Association Kaiho (2009) 706:2-6.
Siemeister et al., "An antagonistic vascular endothelial growth factor (VEGF) variant inhibits VEGF-stimulated receptor autophosphorylation and proliferation of human endothelial cells" PNAS USA (1998) 95:4625-4629.
Stancovski et al., "Mechanistic aspects of the opposing effects of monoclonal antibodies to the ERBB2 receptor on tumor growth," PNAS USA (1991) 88:8691-8695.
Stevenson. Characterization of protein and peptide stability and solubility in non-aqueous solvents. Curr Pharm Biotechnol. Sep. 2000; 1 (2): 165-82.
Strawn et al., "Flk-1 as a target for tumor growth inhibition," Cancer Res (1996) 6(15):3540-3545.
The National Institute of Neurological Disorders and Stroke rt-PA Stroke Study Group, "Tissue Plasminogen Activator for Acute Ischemic Stroke" New England Journal of Medicine (1995) 333(24):1581-1587.
Uchiyama, "rt-PA Intraveneous Therapy," Therapeutics (2008) 42(10):1073-1081 (English abstract included).
Ueda et al., "A novel low molecular weight antagonist of vascular endothelial growth factor receptor bindinq: VGA 1155," Mol Cancer Ther (2003) 2(11):1105-1111.

(56) References Cited

OTHER PUBLICATIONS

Valable et al., "VEGF-induced BBB permeability is associated with an MMP-9 activity increase in cerebral ischemia: both effects decreased by Ang-1," J Cereb Blood Flow Metab. (2005) 25(11):1491-504.

Van Regenmortel and Muller, "D-peptides as immunogens and diagnostic reagents" Current Opinion in Biotechnoloay (1998) 9:377-382.

Vanbruggen et al., "VEGF antagonism reduces edema formation and tissue damage after ischemia/reperfusion injury in the mouse brain," J Clin Invest (1999) 104(11):1613-1620.

Walter et al., "Diagnosis and treatment of patients with stroke in a mobile stroke unit versus in hospital: a randomised controlled trial," Lancet Neural (2012) 11 (5):397-404.

Wesolowski et al., "Single domain antibodies: promising experimental and therapeutic tools in infection and immunity" Med. Microbiol. Immunol. (2009) 198(3):157-174.

Wahlgren et al., "Thrombolysis with alteplase 3-4.5 h after acute ischaemic stroke (SITS-ISTR): an observational study," Lancet (2008) 372(9646):1303-1309.

Witkowski et al., "Conversion of a beta-ketoacyl synthase to a malonyl decarboxylase by replacement of the active-site cysteine with glutamine," Biochemistry (1999) 38(36):11643-11650.

Witte et al., "Monoclonal antibodies targeting the VEGF receptor-2 (Flk1/KDR) as an anti-angiogenic therapeutic strategy," Cancer and Metastasis Reviews (1998) 17:155-161.

Wurch et al., "Development of Novel Protein Scaffolds as Alternatives to Whole Antibodies for Imaging and Therapy: Status on Discovery Research and Clinical Validation" Current Pharmaceutical Biotechnoloav (2008) 9:502-509.

Xu and Ou, "Protein tyrosine phosphatases in the JAK/STAT pathway" Front. Biosci. (2008) 13:4925-4932.

Yoshino et al., "Functional Evaluation and Characterization of a Newly Developed Silicone Oil-Free Prefillable Syringe System," J Pharm Sci (2014) 103:1520-1528.

Yu et al., "Interaction between bevacizumab and murine VEGF-A: a reassessment," Investiqative Ophthalmoloqy & Visual Science (2008) 49(2):522-527.

Zhang et al., "Early VEGF inhibition attenuates blood-brain barrier disruption in ischemic rat brains by regulating the expression of MMPs," Mol Med Rep (2017) 15(1):57-64.

Zhang et al., "Vascular endothelial growth factor and angiopoietins in focal cerebral ischemia," Trends Cardiovasc Med (2002) 12(2):62-66.

Zhang et al., "VEGF enhances angiogenesis and promotes blood-brain barrier leakage in the ischemic brain," J. Clin. Invest (2000) 106(7):829-838.

Zhou et al., "S10013 as a biomarker for differential diagnosis of intra cerebral hemorrhage and ischemic stroke," Neural Res (2016) 38(4):327-332.

Zuo et al. Increased Risk of Cerebrovascular Events in Patients with Cancer Treated with Bevacizumab: A Meta-Analysis. PLoS One. 2014; 9(7): e102484.

* cited by examiner

DRUG REGIMEN FOR TREATMENT OF CEREBRAL ISCHEMIA

CROSS-REFERENCE TO RELATED APPLICATION

This application is a divisional of U.S. application Ser. No. 16/842,458, filed 7 Apr. 2020, which is allowed, and which is a continuation of U.S. application Ser. No. 15/859,075, filed 29 Dec. 2017, now U.S. Pat. No. 10,617,756, issued 14 Apr. 2020, and which claims priority to U.S. provisional application Ser. No. 62/442,826, filed 5 Jan. 2017 and Ser. No. 62/470,086, filed 10 Mar. 2017, each of which are incorporated herein by reference in their entirety.

TECHNICAL FIELD

The invention relates to the field of biological markers for physiological conditions. to treat patients experiencing cerebral ischemia who are at risk for hemorrhagic transformation after pharmacologic or mechanical thrombolysis and to kits for performing the method. In particular, the present invention relates to an effective dose of an inhibitor of vascular endothelial growth factor (VEGF) receptor-mediated signal transduction (VEGF-RST) that provides transient rather than chronic inhibition. The present invention also relates to stabilization of protein drugs to eliminate the need for refrigerated storage, and to packaging of these drugs in a manner that reduces oxygen radical damage and that reduces protein aggregation upon delivery by injection. The invention also relates to improvements in mechanical thrombolysis.

BACKGROUND ART

PCT application PCT/JP2010/062631, published as WO2011/013668 and filed as a continuation-in-part in the United States as U.S. Ser. No. 13/359,281, now U.S. Pat. Nos. 8,652,476 and 9,439,961, describes an improved method to treat cerebral infarction or ischemia in humans by administering a combination of a thrombolytic intervention and an inhibitor of VEGF-RST during the acute stage of the cerebral ischemic event which is considered to be within 6 hours after the onset of the cerebral infarction. This extends the window for treatment from 3 hours to 6 hours.

Supplying an agent that inhibits VEGF-RST ameliorates the hemorrhagic impact of a thrombolytic agent within the enhanced time window for such treatment. This treatment expands the eligible population for thrombolytic therapy, including expanding the time window in which the benefits of administering a thrombolytic outweighs the risks. These documents, however, indicate the dosage level of the VEGF-RST inhibitor is not restricted and suggests high dosages for inhibitors that are anti-VEGF antibodies—in the range of those used to treat cancer.

Studies with regard to such protocols have been published. Zhang, Z. G., et al., *J. Clin. Invest.* (2000) 106:829-838 administered antibody that binds VEGF early (1 hour) and late (48 hours) after stroke induction in a rat model. Using a Harvard pump (Harvard Apparatus; South Natick, Massachusetts, USA), rhVEGF$_{165}$ (Genentech Inc., San Francisco, California USA) was infused intravenously to rats at a dose of 1 mg/kg over a 4-hour interval. Early administration was deleterious while late administration was beneficial. The dose level of antibody against VEGF required for ameliorating the toxicity of tPA was based on a polyclonal antibody RB-222: Kanazawa, M., et al., *J Cereb Blood Flow Metab* (2011) 31:1461-74. A later study was also based on polyclonal antiserum and shows attenuation of BBB disruption by regulating expression of MMP. Zhang, H-T., et al., *Mol Med Rep.* (2017) 15:57-64.

The time of the onset of cerebral infarction is typically difficult to determine as the subject is not under medical supervision at that time. In addition, presence of a disrupted blood-brain barrier (BBB) in a subject with embolic stroke is a risk factor for hemorrhage after thrombolysis. As described by the present inventors in WO2015/138974, determination of both severity and the period of disturbance of BBB integrity can be accomplished by employing a marker for BBB integrity that is present in the blood. A suitable marker is described in a paper by Marchi, N., et al., *Res. Neurol. Neurosci.* (2002) 20:1-13, in their corresponding patents U.S. Pat. Nos. 7,144,708 and 6,884,591 and their later PCT application published as WO2012/154889. These documents describe methods for diagnosing blood-brain barrier permeability in a subject comprising measuring the total level of S100B or its homodimer in the blood wherein elevated levels of S100B or its homodimer indicate BBB permeability. See also Zhou, S., et al., *Neurolog. Res.* (2016) 38:327-332.

A variety of thrombolytic interventions is described in the literature as is a variety of methods to inhibit VEGF-RST. For example, the thrombolytic intervention may include a plasminogen activator such as tissue plasminogen activator (tPA), urokinase, streptokinase or their analogs, other plasminogen activators such as that derived from vampire bats, or from fungi, such as SMTP-7 or mechanical destruction or removal of the embolus. The inhibitor of VEGF-RST may be a specific binding partner for VEGF or VEGF-R or a compound that inhibits the release of VEGF from platelets or a compound that disrupts signal transduction from activated VEGF-R, such as a tyrosine kinase inhibitor.

The most severe strokes also benefit the most from thrombolytic therapy. However, severe strokes are also at higher risk for disruption of the BBB, with tPA exacerbating that disruption. Accordingly, thrombolytics like tPA are currently used in only a few percent of stroke patients due to the risk of hemorrhage, which is exacerbated when given more than 3 hours after the stroke. With adjunct therapy available to reduce the toxicity of tPA, the patient population that can benefit from such treatment is considerably increased. This extends to patients with "wakeup" stroke as recent studies have shown that typically the stroke occurs just before waking. Rubin, M. W., et al, *The Neuro Hospitalist* (2015) 5:161-172.

Currently, the assessment of appropriateness of tPA use is made following a CT scan at the hospital, resulting in substantial delay in treatment compared to the optimal early administration of thrombolytic agents. In studies using an ambulance equipped with a portable CT scanner to reduce the delay in diagnosis, substantial reduction in the time required to select thrombolytic intervention was achieved over standard of care, with no increase in adverse events; Walter, S., *Lancet Neurology* (2012) 11:397-404; Ebinger, M., *JAMA* (2014) 311:1622-1631. While this work has established the utility of early intervention based on improved diagnostic technology, the cost of equipping all ambulances with a CT scanner is prohibitive. The development of an assay that is suitable for point of care that provides comparable early diagnosis of the potential for tPA to be beneficial creates an opportunity for treating a substantial fraction of stroke patients in an ambulance, prior to arrival at the hospital. The present invention facilitates ambulance based treatment. With this improved diagnostic method, the use of thrombolytic agents in patients resulting in desirable therapeutic effects, may increase from less than 5% of putative stroke patients to more than 25%.

The above documents, and all others cited herein are incorporated by reference.

DISCLOSURE OF THE INVENTION

In one aspect, the present invention is directed to a method of treatment to reduce neuronal damage caused by a cerebral ischemic event in a human patient said method comprising administering to said patient an effective amount of a thrombolytic and an effective dose of an inhibitor of vascular endothelial growth factor (VEGF) receptor-mediated signal transduction (VEGF-RST) wherein the effective dose of said inhibitor provides acute inhibition but does not inhibit long term. Typically the effective amount of inhibitor is in the range of 0.1 to 5% of the dose used to treat cancer.

Use of VEGF-RST inhibitors in the stroke context at an appropriate dose level provides an efficient path to reducing tPA toxicity. Since the goal in this context is acute blockage of VEGF activity, the dose required is qualitatively less than the dose used to treat cancer for which extended pharmacological activity is desired. Normal clearance of a low dose of a VEGF-RST inhibitor will assure its decline below pharmacologically active levels well before the longer term remodeling phase for which VEGF is a beneficial factor.

With respect to VEGF-RST inhibitors, antibodies to VEGF are currently in use for treatment of cancer, wherein long term suppression of VEGF activity is desired and the dose is based on achieving an efficacious blood level for several weeks. For the amelioration of toxicity of thrombolytics in stroke patients, only short term suppression is needed (ideally, 48 hours). Similarly, other VEGF-RST inhibitors, such as kinase inhibitors that include, for example, Sutent®, are also used for cancer treatment, where chronic treatment is needed.

In another aspect, the invention is directed to a suite of factors that permits point-of-care treatment of patients experiencing cerebral ischemia, including treatment during transport by ambulance. The innovations provided by the present invention include, in addition to adjusting the dose of inhibitors of VEGF-RST, stabilizing the drugs to be administered by suitable packaging and stabilization techniques, and determining the suitability of the patient for the treatment suggested by assessing markers in the blood for indication of the breakdown of the blood-brain barrier (BBB).

As to storage the combination for the treatment typically comprises two biologics, a thrombolytic agent and an inhibitor of VEGF-RST, such as an antibody against vascular endothelial growth factor receptor (VEGF), or an inhibitor of tyrosine kinases (which mediate signaling by VEGF-R) to reduce the incidence or severity of hemorrhage. Thus, stabilization is required. The dose of thrombolytic is based on standard of care. According to the invention, the dosage of the VEGF-RST is much lower than that used in cancer treatment.

This combination treatment should preferably be administered in cases where the severity of the stroke is sufficient to warrant the risk of treatment with a thrombolytic agent which may cause hemorrhaging even if a preventative as described above—i.e., an inhibitor of VEGF-RST—is administered as well. Thus, in another aspect, the invention is directed—to a method to identify patients suitable for treatment using a point-of-care assay for S100B or S100B dimer in blood.

The invention also is directed to kits that contain reagents for determining one or more biomarkers of BBB disruption and to containers of therapeutic agents in compositions or materials to provide thrombolytic or thrombectomy intervention in conjunction with inhibitors of VEGF-RST. The drugs and reagents in such kits may be provided in measured amounts according to the dosage required.

The invention is also directed to mechanically removing a blood clot associated with said ischemia event and administering, in association with said removing, a measured dose of an inhibitor of VEGF-RST effective to inhibit >50% of signal transduction over 24 hours, especially wherein said inhibitor is administered by means of a catheter that is part of a device for said mechanical removal.

MODES OF CARRYING OUT THE INVENTION

As noted above, in one aspect of the invention, there are three basic aspects that permit effective point-of-care treatment for patients with cerebral ischemia including treatment during transport in an ambulance. These facets are: Adjustment of the dose of an inhibitor of VEGF-RST used in conjunction with a thrombolytic agent; stabilization of the drugs used in this treatment by suitable treatment of the drugs themselves and/or by appropriate packaging; and assessing the appropriateness of treatment including at the point-of-care by determining markers of BBB integrity or breakdown in the blood of the patient.

A critical feature is the dosage level of the VEGF-RST inhibitor. Many such inhibitors are known in the art and used for cancer treatment. For inhibitors of VEGF-RST, an acute dosage is required with the absence of long term inhibition. Antibodies, including those that bind VEGF and VEGF-R inherently show long term effects so a reduced dosage is required as compared to that used for cancer treatment, as is also the case for kinase inhibitors. The same is true of inhibitors of kinases associated with VEGF-R signaling. For any inhibitor of VEGF-RST, the dosage should be such that the inhibition is provided only over 24-48 hours and inhibits VEGF-RST >50% or >60% and not extend appreciably past that window—i.e., unlike cancer treatment which extends over periods of 5 days or more. For antibodies or antigen binding fragment or for kinase inhibitors, this is achieved by using a dose <5% or <1% or <0.1% of that employed for treatment of cancer since the normal elimination from the body will thereby reduce the serum concentration below the pharmacologically active level within the indicated time period. The systemic effects of low dosages are minimal as reported in Avery, R. L., et al., *Br. J. Ophthalmol.* (2014) 98(12):1636-41.

"Antibodies" can encompass Fab fragments, single chain Fv constructs, and bi-specific constructs. The antibodies may be polyclonal or monoclonal and may be recombinantly produced. The antibodies are preferably minimally antigenic in humans and thus may be human by sequence (from a transgenic animal expressing a human antibody repertoire or a recombinant library of human antibody genes), may be humanized, or may be isolated from a human or may be chimeric. Likewise, reduced size (low-molecular-weight) antibodies (nanobodies) such as antibodies (naturally occurring variants) found in camels or sharks are also useable. Antibody mimics include families of proteins based on scaffolds such as: fibronectin, transferrin, glutathione transferase, lens crystallin. Other mimics include small peptides, peptide mimics (for example, incorporating beta amino acids, or D-amino acids, or chemical crosslinkers to increase conformational stability, as well as non-peptide binding agents such as nucleic acid based aptamers.

Examples of anti-VEGF antibodies include ranibizumab (Lucentis®), aflibercept (Eylea®) and bevacizumab (Avastin®). The standard dosage for Avastin® in human patients is in the range of 50 mg. There are many kinase inhibitors—there are at least 240 in common use. See Science (2017) 658:1148. Typical are Tivozanib, Apatinib, Lenvatinib, Axitinib, Imtinib, Motesanib, Fruquitinib, Brivanib, Cediranib, Regorafenib, Sulfatinib, and Sunitinib (Sutent®). Typical dosage of Sutent® for cancer treatment is 50 mg orally daily for 4 weeks, followed by 2 weeks off. Also included as VEGF-RST inhibitors are aptamers that bind kinases or VEGF or VEGF-R, such as Pegaptanib, a pegylated anti-VEGF aptamer.

With respect to thrombolytic agents and interventions, various plasminogen activators could be employed such as tissue plasminogen activator (tPA) or a derivative thereof, urokinase, streptokinase, single-chain urokinase-type plasminogen activator (uPA), desmoteplase (derived from vampire bat plasminogen activator), and other proteases acting on fibrin. Other agents known to cleave fibrin as well as mechanical disruption are also used in the present invention. These may be used alone or in combination.

Briefly, however, this combination of drugs according to the improved method of the invention restricts the dose of the inhibitor of VEGF-RST to doses that exclusively act on an acute basis, i.e., where the drug concentration decreases substantially after 24-48 hours. Doses are <5% of those used for such inhibition when used in the treatment of cancer. The amounts thus useful can be extrapolated from those employed by an inhibitor of VEGF-RST that is an antibody against VEGF. Thus, the blood concentration by the anti-VEGF antibody can be compared to the blood concentration of alternative forms of these inhibitors to determine the suitable dose for any VEGF-RST inhibitor that will act only acutely as defined herein. The combination of drugs administered in the treatment is specifically limited to combinations in which the dose of inhibitor of VEGF-RST is <5%, or <1% or <0.1% of that employed to obtain the desired effects in the treatment of cancer. For small molecule drugs (as well as antibodies or fragments) the dose is in an amount needed to inhibit >50% or >60% of VEGF-RST activity over 24 hours. This means that the monoclonal antibody dosages employed in the present invention protocol are in the range of 0.1-2.5 mg in a 70 kg patient, or 0.5-2.0 mg in a 70 kg patient or 1 mg-1.5 mg in a 70 kg patient with adjustments for patients of different weights.

Administration may be oral or by injection. Intravenous injection is preferred, but not required. The preferred mode of administration will, of course, depend on the specific therapeutic agent employed. Typical vehicles for oral administration include, tablets, capsules, syrups and the like with standard excipients; excipients for injectables are also conventional and well-known in the art. These can be found, for example, in the latest addition of Remington Pharmaceutical Sciences published by Mack Publishing Company, Easton, PA Injection may be by traditional methods or a pneumatic pressure system as marketed by Pharmajet, Golden, Colorado.

The inhibitors of VEGF-RST described above may also be used in conjunction with mechanical thrombolysis which is typically conducted by inserting a catheter and mechanically removing a blood clot that is associated with the ischemia. These inhibitors may be provided separately, or may be introduced by means of the catheter used for the mechanical removal. A multiplicity of devices for mechanical removal of blood clots associated with ischemia is known in the art and these are described hereinbelow. Providing the VEGF-RST inhibitor directly to the clot has the advantage of an acute dosage specifically associated with the clot itself, but additional administration of such inhibitors systemically may be employed instead of, or in addition to, administration via the catheter. In this aspect of the invention, assessment of the status of the blood brain barrier is not required as mechanical removal of the clot does not appreciably enhance the risk of hemorrhage.

However, if the thrombolytic agent is a pharmaceutical, assurance that hemorrhage is unlikely is desirable. Determination of both desirability and timing of administration of thrombolytic agents in an expeditious manner that can be administered in an ambulance can be achieved using a point of care assay for one or more biomarkers in the blood for degree of BBB disruption. For this purpose, a preferred embodiment is measurement of S100B and/or its homodimer in the blood. S100B is a calcium binding protein secreted from astrocytes, for which normal level in peripheral blood is extremely low. Other markers of blood-brain barrier disruption are known in the art, and can be used in place of or in combination with S100B assay. For example, elevated levels of UCHL-1 in the peripheral blood are diagnostic of BBB disruption. Puvenna, V., et al., *PLoS ONE* (2014) 9(5):e96296.

Diagnostics using blood have traditionally been limited to laboratory use because they rely on sophisticated instruments, are time and labor intensive, and require sample purification. Progress in the combined fields of biosensors and microfluidics enables a point of care diagnostic. Luka, G., et al., *Sensors* (2015) 15:30011-30031. A biosensor incorporates a biologically derived recognition element, such as an antibody, immobilized on a physicochemical transducer. Microfluidic systems control the flow conditions, increase the mixing rate of different reagents, and reduce sample volume (down to nanoliter scale), thereby increasing sensitivity of detection while also providing sample preparation capabilities.

Point-of-care assay for severity of BBB disruption such as a blood-borne marker is useful to allow prompt thrombolytic therapy, thereby achieving higher efficacy, with risk of adverse hemorrhage reduced by combination with an agent for blocking VEGF activity.

The use of a point of care assay for BBB disruption, and thus, an evaluation of desirability and timing of treatment, offers an improvement in relation to the treatment described in the above-referenced WO2011/013668 which is incorporated herein by reference.

U.S. Pat. Nos. 6,884,591 and 7,144,708, incorporated herein by reference with respect to conduct of the assays described, describe assays for the behavior of BBB integrity subsequent to cerebral ischemia. As outlined in the '591 and '708 patents, measurement of S100B in the blood (or plasma or serum) has the advantage that its levels are normally very low or undetectable in blood with normal levels being 0.05 ng/ml, increasing 10 to 100-fold upon damage to the BBB. The range of S100B levels that is readily detectable by various point of care assay platforms is 1 ng/ml to about 1 mg/l. Thus, increases above the normal level can readily be measured.

In the foregoing methods, to maximize the utility of this strategy, it is important for the thrombolytic agent and the inhibitor of VEGF-RST to be readily available prior to arrival at a hospital. Since a refrigerated or other cold storage method for these sensitive protein drugs is difficult to provide in the confines of an ambulance, it is further advantageous to stabilize these biologic drugs in a manner that eliminates the need for refrigerated storage. Several strategies are available for this purpose. There is of course no reason such stabilized and packaged drugs and the assays and treatment regimen of the invention could not be used in a hospital setting.

Protein stabilization to eliminate the need for refrigeration has been of great interest in the context of vaccines, particularly for use in tropical countries. Lyophilization conditions have been found that result in extended shelf life without refrigeration, along with easy dissolution into sterile saline. U.S. Pat. No. 8,313,897 discloses utility of certain sugars along with polyethyleneimine in a lyophilized form. U.S. Pat. No. 7,153,472 discloses achieving a powdered glass (amorphous, semi-crystalline) composition via vaporization foam drying (more rapid than conventional lyophilization and less prone to protein denaturation). Further details of foam drying are disclosed in U.S. Pat. No. 5,766,520. In addition to protein stabilization, syringe design has an impact on formation of microaggregates, as described in Yoshino, K., et al., (2014) *J. Pharm. Sci.* 103:1520-1528. With appropriate coating technology, smooth dispensing is feasible without use of silicone oil that can promote protein microaggregation.

In summary, the invention provides improvements that permit emergency treatment of ischemic patients in an ambulance setting as well as improvements in procedures that are typically performed in a hospital. Thus, materials and methods were provided for assessing the appropriate emergency treatment with a therapeutic agent that dissolves clots while minimizing the risk of hemorrhage by assessing the status of the blood brain barrier and administering a VEGF-RST inhibitor in an appropriate amount. The invention is also directed to improving the outcome of mechanical clot removal by administering such inhibitors in similar amounts, especially in the same catheter as employed in the mechanical removal.

The following examples illustrate but do not limit the invention.

Example 1

Assay to Evaluate Combined Administration of tPA and Anti-VEGF Antibody as a Function of Treatment Window A cerebral infarction rat model is disclosed in the above-referenced WO2011/013668 and U.S. Pat. Nos. 8,652,476 and 9,439,961. Briefly, a thrombus is formed by coagulating autologous blood from rats and thrombin as a gel in a polyethylene tube catheter. This is allowed to stand overnight and cut to have a length of 1 mm. The thrombus is injected from the external carotid artery into the middle cerebral artery of the rat model under anesthesia with halothane. Cerebral blood flow is measured before and 30 minutes or 24 hours after injection of the thrombus. Animals exhibiting a cerebral blood flow lower than 50% of that measured before injection of the thrombus are used as models in the experiments.

After injection of the thrombus, BBB status is assessed by comparing the serum S100B level as a function of time as compared to the S100B level measured prior to injection of the thrombus. The anti-VEGF treatment markedly reduces the S100B level normalized against the level in the same individual rat prior to the induced stroke. The efficacy is seen at both time points (3-9 hours and 24 hours following the induced stroke with 4 out of 5 rats showing decreased S100B in the anti-VEGF group compared to only one in the control group.

Example 2

Measurement of VEGF and S100B in Human Stroke Thrombus Samples

A review of multiple S100B studies concluded that it is not suitable as a marker of stroke in general, but is useful as a surrogate marker for cerebral damage (Dassan, P., et al., *Cerebrovasc. Dis.* (2009) 27:295-302). The use of tPA combined with an agent to ameliorate tPA toxicity by blocking VEGF signaling is most appropriate for patients with more severe cerebral damage, for which S100B is a useful marker for selecting patients to receive this combination therapy.

Currently, tPA is the only pharmacological intervention widely used to dissolve intra-arterial clots, helping to restore cerebral blood flow. Other interventional strategies include the use of tools that mechanically disrupt and remove intra-arterial clots, notably including: MERCI® or Trevo® (Stryker; Kalamazoo, MI); Solitaire™ (Medtronic; Minneapolis, MN); Apollo™ (Penumbra; Alameda, CA). To test whether the same local elevation of VEGF observed in the rat model was present in human brain after an embolic stroke event, 39 patients were enrolled for this study. Of these, 18 received tPA intravenously before interventional thrombectomy was initiated. All patients underwent endovascular recanalization procedure with 20 cases classified as hemorrhagic by clinical and radiologic criteria. Extent of stroke by MlI was measured as diffusion weighted imaging (DWI) and quantified by a modified Alberta Stroke Program Early CT score (ASPECTS). European Cooperative Acute Stroke Study (ECASS) criteria were used to define the nature of the hemorrhage. The extracted thrombus and aspirate are normally discarded, but in this study were saved for analysis. Full recanalization was achieved in 50% of cases, partial success was achieved in 25% of interventions. The values of S100B and VEGF were not statistically correlated with the success or extent of recanalization. Peripheral blood samples were also collected and assayed for VEGF or S100B by ELISA assay. Analyte levels did not depend on the mechanism of stroke etiology (atherosclerotic, 7%; cardioembolic, 56%; large vessel occlusion, 15%; cryptogenic, 22%).

When values of circulating VEGF were compared to levels of tPA in clot, there was a statistically significant correlation between tPA levels and VEGF ($P<0.006$). After partitioning the patients as $VEGF_{Clot}>VEGF_{Peripheral}$, it was observed that only 42% of patients with low VEGF experienced a hemorrhage (determined by CT scans), while 72% of patients with elevated brain VEGF were affected by hemorrhage (difference between groups $P=0.05$). The relationship between peripheral S100B and presence of hemorrhage was significant ($P<0.05$) and did not depend on the method used (CT or MRI). When all patients were analyzed together, S100B and VEGF in clot correlated well with radiologic endpoints; clot VEGF and peripheral S100B were specifically correlated with poor outcome (Discharge NIH stroke scale (NIHSS)).

Based on the human data above, a further experiment in the rat experimentally induced intra-arterial thrombotic model was performed to examine S100B after treatment with a rabbit polyclonal anti-VEGF antibody. In untreated animals, 80% showed increased S100B in serum at 8 and 24 hours following ischemic stroke (normalized to previous day baseline level). By contrast, 80% of the anti-VEGF treated animals had marked reductions in S100B at both time points.

Example 3

Dose Adjustment for Antibody Against VEGF

The effective amount of an inhibitor of VEGF-RST is determined from available sources as follows: Studies establishing the utility of an antibody against VEGF for ameliorating the hemorrhagic activity of tPA used a polyclonal rabbit serum designated RB-222 (Thermo Fisher): Kanazawa, M., et al., *J. Cerebral Blood Flow and Metabolism* (2011) 31:1461-1474. The dose given to rats was 30 or 100 ug/rat; in Zhang, H-T., et al., *Mol Med Rep.* (2017) 15:57-64, a dose of RB-222 of 10 ug/rat was more efficacious than 5 ug/rat. With a weight of 500-1000 g, these results imply an effective dose was ~75 ug/kg. Applied to humans, with an average weight of 70 kg, this corresponds to providing ~5 mg dose to a person. A standard commercial single dose vial of the anti-VEGF antibody Avastin® (bevacizumab, Genentech) contains 100 mg with multiple vials used to achieve the recommended 10-15 mg/kg total dose. While this dose is appropriate for cancer treatment, the foregoing Kanazawa and Zhang data demonstrate an effective dose for combination with thrombolysis in treatment of stroke is only ~5 mg per patient if a polyclonal such as RB-222 is employed. For the stroke indication described here, the appropriate dose for the combination treatment is ~1% of the dose used for cancer.

The $EC_{50}$ of Avastin® binding to VEGF in an in vitro ELISA assay is 0.1 ug/mL. The vendor's recommended concentration of RB-222 for the closely related immunohistochemistry application is 10 ug/mL. That is, the monoclonal antibody is 100-fold more potent than the polyclonal serum in vitro. The equivalent human dose for the acute stroke indication by this comparison is thus 1% of the dose used for cancer.

Example 4

Dose Adjustment Based on Pharmacokinetics

A PK model was constructed using published data on low dose Avastin® arising from spillage into systemic circulation from the antibody given intra-ocularly to treat macular degeneration Avery R. L., *Br. J. Ophthalmol.* (2014) 98:1636-41. Assay of VEGF in an extracted clot following thrombectomy showed that the peak concentration at that site is ~10 nM. The published Kd of Avastin® for VEGF is 2.2 nM, and the model predicts that Avastin® at ~1 nM (0.15 μg/ml) will be sufficient to sequester the peak VEGF level in the clot.

This concentration of antibody (~1 nM) across 5 L of blood is achieved with a dose of 0.01 mg/kg, or 0.7 mg for a 70 kg person. This is 0.1% of the standard cancer dose. At that dose, the normal clearance reduces the antibody concentration to <10% of its Kd within 48 hours after which it will have negligible pharmacological activity.

In a murine model, this is borne out. A dosage range of $2.67 \times 10^{-3}$ mg/kg to $8.8 \times 10^{-3}$ mg/kg Avastin® IV gave peak blood levels $1.5 \times 10^{-4}$-$49 \times 10^{-4}$ 82 g/ml or 6-18 nM. This was sufficient to depress VEGF levels in serum from 22 pg/ml to 10 pg/ml.

The invention claimed is:

1. A method of treatment to reduce neuronal damage caused by a cerebral ischemic event in a human patient, said method comprising administering to said patient an effective amount of a thrombolytic agent and an effective amount of an inhibitor of vascular endothelial growth factor (VEGF) receptor-mediated signal transduction (VEGF-RST), wherein
   (i) the inhibitor is selected from the group consisting of ranibizumab and bevacizumab, and wherein the effective amount of the inhibitor is 0.1-2.5 mg in a 70 kg patient with adjustments for patients of different weights;
   (ii) the effective amount of said inhibitor provides inhibition of >50% of said VEGF-RST activity over 24 hours; and
   (iii) the serum concentration level of said inhibitor is reduced below this pharmacologically active level at least by 48 hours after administration.

2. The method of claim 1, which further includes conducting an assay for blood-brain barrier (BBB) integrity loss resulting from said ischemic event.

3. The method of claim 2, wherein the assay comprises measuring total S100B and/or S100BB homodimer in the blood.

4. The method of claim 1, wherein said thrombolytic agent comprises tissue plasminogen activator (tPA), urokinase, streptokinase, desmoteplase, single chain urokinase-type plasminogen activator (uPA).

5. The method of claim 1, wherein the thrombolytic agent and the inhibitor of VEGF-RST are formulated and/or packaged for long term stability at room temperature.

6. The method of claim 1, wherein the effective amount of the inhibitor is 0.5-2.0 mg in a 70 kg patient with adjustments for patients of different weights.

7. The method of claim 1, wherein the effective amount of the inhibitor is 1-1.5 mg in a 70 kg patient with adjustments for patients of different weights.

8. A method of treatment to reduce neuronal damage caused by a cerebral ischemic event in a human patient, said method comprising mechanically removing a blood clot associated with said ischemia event and administering in association with said removing a measured dose of an inhibitor of VEGF-RST, wherein:
   the inhibitor is selected from the group consisting of ranibizumab and bevacizumab, and wherein the effective amount of the inhibitor is 0.1-2.5 mg in a 70 kg patient with adjustments for patients of different weights; and
   the inhibitor is effective to inhibit >50% of signal transduction over 24 hours and wherein the serum concentration level of said inhibitor is reduced below this pharmacologically active level at least by 48 hours after administration.

9. The method of claim 8, which is performed by a device comprising a catheter for said mechanical removal and wherein said inhibitor is administered by means of a catheter that is part of a device for said mechanical removal.

10. The method of claim 8, wherein the effective amount of the inhibitor is 0.5-2.0 mg in a 70 kg patient with adjustments for patients of different weights.

11. The method of claim 8, wherein the effective amount of the inhibitor is 1-1.5 mg in a 70 kg patient with adjustments for patients of different weights.

* * * * *